United States Patent [19]
Gast et al.

[11] Patent Number: 6,146,429
[45] Date of Patent: Nov. 14, 2000

[54] CARRIER COMPOSITION FOR OXIDATIVE DYEING OF HAIR AND METHOD OF DYEING HAIR USING SAME

[75] Inventors: Anette Gast, Weiterstadt; Petra Braun, Muenster; Wolfgang R. Balzer, Alsbach; Herbert Deutz, Gross-Umstadt, all of Germany

[73] Assignee: Wella Aktiengesellschaft, Darmstadt, Germany

[21] Appl. No.: 09/068,597

[22] PCT Filed: Jul. 5, 1997

[86] PCT No.: PCT/EP97/03554

§ 371 Date: May 11, 1998

§ 102(e) Date: May 11, 1998

[87] PCT Pub. No.: WO98/11863

PCT Pub. Date: Mar. 26, 1998

[30] Foreign Application Priority Data

Sep. 18, 1996 [DE] Germany ............... 196 37 966

[51] Int. Cl.⁷ .................................................. A61K 7/13
[52] U.S. Cl. ................ 8/408; 8/406; 8/407; 8/563; 8/580; 8/597
[58] Field of Search ............... 8/405, 406, 408, 8/580, 563, 407, 597; 132/208; 424/70.6, 70.7

[56] References Cited

U.S. PATENT DOCUMENTS

| | | | |
|---|---|---|---|
| 3,861,868 | 1/1975 | Milbrada et al. | 8/410 |
| 5,110,318 | 5/1992 | Altobelli et al. | 8/405 |
| 5,154,916 | 10/1992 | Arradeau et al. | 424/63 |
| 5,449,403 | 9/1995 | Andrean et al. | 8/405 |
| 5,451,254 | 9/1995 | Andrean et al. | 8/405 |
| 5,496,543 | 3/1996 | Lagrange et al. | 424/70.7 |
| 5,616,746 | 4/1997 | Mahieu et al. | 554/66 |
| 5,665,778 | 9/1997 | Semeria et al. | 514/613 |
| 5,720,943 | 2/1998 | Mougin et al. | 424/70.7 |
| 5,747,013 | 5/1998 | Mougin et al. | 424/70.7 |
| 5,753,215 | 5/1998 | Mougin et al. | 424/70.7 |
| 5,858,339 | 1/1999 | Piot et al. | 424/70.7 |

FOREIGN PATENT DOCUMENTS

| | | |
|---|---|---|
| 0 186 025 A2 | 7/1986 | European Pat. Off. . |
| 0 471 606 A2 | 2/1992 | European Pat. Off. . |
| 47-045502 | 11/1972 | Japan . |
| 47-047666 | 12/1972 | Japan . |
| 1-165514 | 6/1989 | Japan . |

OTHER PUBLICATIONS

G. Schrader: "Grundlagen Und Rezepturen Der Kosmetika", pp. 172–173 and 555–558 (1989). (No Month Available).
Derwent Abstract of JP 01–165514A, Dec. 22, 1987.

*Primary Examiner*—Carloine D. Liott
*Attorney, Agent, or Firm*—Michael J. Striker

[57] ABSTRACT

The dye carrier composition for oxidative dyeing of hair advantageously includes a combination of about 0.01 to 5 percent by weight of developer substance and about 0.01 to 5 percent by weight of coupler substance, from 0.1 to 10 percent by weight beeswax and from 0.1 to 10 percent by weight of one or more protein hydrolyzates and/or amino acids. The composition can also contain 0.1 to 30 weight percent of an non-ionic and/or anionic wetting agent or emulsifier and the protein hydrolyzates preferably include silk protein hydrolyzate and/or keratin hydrolyzate.

9 Claims, No Drawings

CARRIER COMPOSITION FOR OXIDATIVE DYEING OF HAIR AND METHOD OF DYEING HAIR USING SAME

BACKGROUND OF THE INVENTION

1. Field of the Invention

The invention relates to dye carrier compositions for oxidative or non-oxidative coloring of hair, particularly human hair, which contain a combination of beeswax and protein hydrolyzates and/or amino acids.

2. Prior Art

For coloring hair, either direct colorants or oxidative colorants are used which are created through oxidative coupling with one or a plurality of developer components or with one or a plurality of coupler components, or with a mixture of these colorants. As a rule, oxidative colorants allow for an intensive coloring with good natural characteristics; however, the development of the colors takes place under the influence of strong oxidative solutions, for example hydrogen peroxide, which frequently leads to damage of the fiber. Although direct colorants are applied under more protective conditions, the resulting color effect is frequently not satisfactory, particularly with regard to the color balance of damaged and non-damaged hair.

SUMMARY OF THE INVENTION

It is therefore the object to make a hair dye carrier composition available that is easy to apply, offers good conditioning and creates the least possible damage to the hair, as well as allowing for a balanced color effect regardless of the different hair textures.

For this purpose it has now been discovered that a hair coloring agent containing a combination of beeswax and protein hydrolyzate and/or amino acids achieves the present object in an excellent manner.

The subject of the present invention is a dye carrier composition for coloring hair based on a developer-coupler substance combination and/or direct colorants, characterized in that it contains a combination of (a) beeswax and (b) at least one protein hydrolyzate and/or at least one amino acid.

The beeswax is used in the agent in accordance with the invention in a quantity of 0.1 to 10 weight-percent, preferably 0.5 to 5 weight-percent.

Protein hydrolyzates used are preferably silk protein hydrolyzates, keratin hydrolyzates or a mixture thereof, while for the use of amino acid, neutral as well as acidic or alkaline amino acids can be used, such as glycine, alanine, valine, leucine, glutaminic acid and arginine.

The quantity of protein hydrolyzate and/or amino acid contained in the agent in accordance with the invention is preferably 0.1 to 10 weight-percent, particularly 0.5 to 5 weight-percent. The use of a combination of one or more protein hydrolyzates with one or a plurality of amino acids is particularly preferred.

As direct-dyeing or direct dye compounds common, physiologically harmless, direct-dyeing or direct dye compounds selected from the group of nitro dye compounds azo dye compounds, quinone dye compounds and triphenyl-methane dye compounds can be used, such as 4,N-ethyl,N-(2'-hydroxyethyl)amino-1-(2"-hydroxyethyl)amino-2-nitrobenzene, 1-amino-3-methyl-4-(2'-hydroxyethyl)amino-6-nitrobenzene, 2,2'-[(amino-3-nitrophenyl)imino]-bis-ethanol hydrochloride (HC Red 13), 1-(2'-hydroxyethyl)amino-2-nitro-4-bis-(2"-hydroxyethyl)aminobenzene, 4-bis-(2'-hydroxyethyl)amino-1-(2"-methoxyethyl) aminonitrobenzene, 1-(2',3'-dihydroxypropyl)amino-2-nitro-4-[methyl-(2"-hydroxyethyl)amino]benzene, 1-[(2', 3'-dihydroxypropyl)amino]-2-nitro-4-[ethyl-2"1-(hydroxyethyl)amino]benzene, 1-(3'-hydroxypropylamino)-2-nitro-4-bis-(2"-hydroxyethylamino)benzene, 1-amino-4-(2'-hydroxyethyl)-aminonitrobenzene, 1-hydroxy-2-amino-4,6-dinitrobenzene, 1-amino-2-nitro-4-bis-(2'-hydroxyethyl)aminobenzene, 1-amino-2-nitro-4-(2'hydroxyethyl)amino-5-chlorobenzene, 1-(2'hydroxyethyl) amino-2-nitro-4-aminobenzene, 1-hydroxy-3-nitro-4-aminobenzene, 1-(2'aminoethyl)amino-2-nitro-4-(2"-hydroxyethyl)-oxybenzene, 3-nitro-4-(2'-hydroxyethyl) aminophenylglycerine ether, 1-amino-5-chloro-4-(2',3'-dihydroxypropyl)amino-2-nitrobenzene, 1,4-bis-[(2',3'-dihydroxypropyl)amino]-5-chloro-2-nitrobenzene, 1-hydroxy-2-(2'hydroxyethyl)amino-4,6-dinitrobenzene, 2-amino-6-chloro-4-nitrophenol, 1-hydroxy-3-nitro-4-(3-hydroxypropylamino)benzene, 3-nitro-4-ethylaminobenzoic acid, 4-amino-2-nitrodiphenylamino-2-carboxylic acid, 2-chloro-6-ethylamino-4-nitrophenol, 2,5-diamino-6-nitropyridine, 1,2,3,4-tetrahydro-6-nitroquinoxaline, 4-(2'-hydroxyethyl)amino-3-nitrobenzonitrile, 4-(2'-hydroxyethyl)amino-3-nitrobenzamide, 3-amino-2-(2'-hydroxyethyl)amino-5-nitrobenzene, 1-methoxy-2-(2'-hydroxyethyl)amino-5-nitrobenzene, 1-hydroxy-3-nitro-4-(2"-hydroxyethyl)aminobenzene, 1-hydroxy-2-amino-3-nitrobenzene, 1-amino-2-methyl-6-nitrobenzene, 1-(2'-hydroxyethyl)-oxy-3-methylamino-4-nitrobenzene, 1-methylamino-2-nitro-5-(2',3'-dihydroxypropyl)-oxybenzene, 1-(2'-hydroxyethyl)amino-2-hydroxy-4-nitrobenzene, 1-methoxy-3-(2'-amino-ethyl)-amino-4-nitrobenzene, 1-(2'-ureidoethyl)amino-4-nitrobenzene, 1-(2'-hydroxyethyl)amino-2-nitrobenzene, 4-(2'-hydroxyethyl)amnino-3-nitrotrifluoromethylbenzene, 2,4-bis-[N-(2'-hydroxyethyl)amino]-5-chloronitrobenzene, 4-(2', 3'-dihydroxypropyl)amino-3-nitrotrifluoromethylbenzene, 4-(2'-hydroxymethyl)amino-3-nitromethylbenzene, 4-(2'-hydroxyethyl)amino-3-nitrochlorobenzene, 1-(nitrophenylazo)-2-methyl-4-bis-(2"-hydroxyethyl)aminobenzene, 1-(3'-nitro-4-amino) phenylazo-2-hydroxy-7-trimethylammonium chloride naphthalene, 1-(2'-hydroxy-4'-sulfo-6'-nitro)-naphthylazo-2-hydroxynaphthalene, 1-(4'-aminophenylazo)-2-methyl-4-bis-[(2'-hydroxyethyl)amino]benzene, 4-(4'-dimethylaminophenylazo)-1-4-dimethyltriazonium chloride, 1-(2'-methoxyphenylazo)-2-hydroxy-7-trimethylammonium naphthalene chloride, 1-(4'-aminophenylazo)-2-hydroxy-7-trimethylammonium naphthalene, 4-(3'-trimethylammoniumphenylazo)-N-phenyl-3-methylpyrazolone(5), 4-hydroxy-3-[(4'-sulfo-1'-naphthyl)azo]-1-naphthalenesulfonic acid, 1-(4'-sulfophenylazo)-2-hydroxynaphthalene, 1-(4'-sulfonephenylazo)-2-hydroxy-6-sulfonaphthalene, 4-amino-[4'-bis-(2"-hydroxyethyl)amino]azobenzene, 4-amino-[4'-bis-(2"-hydroxyethyl)amino]-2'-methylazobenzene, 3-(2',6'-diaminopyridyl-3'-azo)pyridine, 7-phenylazo-1-amino-3,6-disulfo-8-hydroxynaphthalene, 5-acetylamino-4-hydroxy-3-[2'-methylphenyl)azo]-2,7-naphthalenedisulfonic acid, 2'-(2', 41-dimethylphenylazo)-6-(4"-sulfophenylazo)-1,3-dihydroxybenzene, 1,4-bis-(2',3'-dihydroxypropyl) aminoanthraquinone, 1-methylamino-4-(2'-hydroxyethyl) aminoanthraquinone, 2-(2'-aminoethyl) aminoanthraquinone, 2-bromo-4,8-diamino-6-(3'-trimethylammonium)phenylamino-1,5-naphthoquinone, 1-(2'-trisulfo-4'-methylphenyl)amino-4-hydroxyanthraquinone, 1,4-diaminoanthraquinone, 1-amino-2-sulfo-4-cyclohexylaminoanthraquinone, 1-methylamino-4-aminopropylaminoanthraquinone, 1-aminopropylaminoanthraquinone, 4',4'',4'''-triamino-3-methyltriphenylcarbonium chloride, bis-(4,4-diethylaminophenyl)-4'-ethylaminonaphthylcarbonium chloride, bis-(4,4-dimethylaminophen)-4'-phenylaminonaphthylcarbonium chloride and 4,4-bis-(N-ethyl-3-sulfobenzyl)-amino-2''-sulfofuchsonium, 2,4-dinitro-1-naphthol-7-sulfonic acid disodium salt (Acid Yellow 1; C.I. 10 316); 2-(2'-quinolyl)-1H-indene-1,3(2H)-dione monodisulfonic acid disodium salt (Acid Yellow 3; C.I. 47 005); 4,5-dihydro-5-oxo-1-(4'-sulfophenyl)-4-[(4''-sulfophenyl)azo]-1H-pyrazole-3-carboxylic acid trisodium salt (Acid Yellow 23; C.I. 19 140); 3',6'-dihydroxyspiro[isobenzenefurane-1(3H),9'(9H)-xanthen]-3-one (Acid Yellow 73; C.I. 45 350:1); 5-[2', 4'-dinitrophenyl)amino]-2-(phenylamino)benzenesulfonic acid sodium salt (Acid Orange 3, C.I. 10 385); 4-[2', 4'-dihydroxyphenyl)azo]benzenesulfonic acid sodium salt (Acid Orange 6; C.I. 14 270); 4-[2'-hydroxy-1'-naphthyl)azo]benzenesulfonic acid sodium salt (Acid Orange 7; C.I. 15 510); 4-[[3'-[(2'',4''-dimethylphenyl)azo]-2',4'-dihydroxyphenyl]azo]benzenesulfonic acid sodium salt (Acid Orange 24; C.I. 20 170); 4-hydroxy-3-[(4'-sulfo-1'-naphthyl)azo]-1-naphthalenesulfonic acid disodium salt (Acid Red 14; C.I. 14 720); 7-hydroxy-8[(4'-sulfonaphthyl)azo]-1,3-naphthalenedisulfonic acid trisodium salt (Acid Red 18; C.I. 16 255); 3-hydroxy-4-[(4'-sulfo-1'-naphthyl)azo]-2,7-naphthalenedisulfonic acid trisodium salt (Acid Red 27; C.I. 16 185); 5-amino-4-hydroxy-3-phenylazo-2,7-naphthalenedisulfonic acid disodium salt (Acid Red 33; C.I. 17 200); 5-(acetylamino)-4-hydroxy-3-[(2'-methylphenyl)azo]-2, 7-naphthalenedisulfonic acid disodium salt (Acid Red 35; C.I. 18 065); 3', 6'-dihydroxy-2',4',5',7'-tetraiodospiro[isobenzofurane-1(3H),91(9H)-xanthen]-3-one disodium salt (Acid Red 51, C.I.45 430); 3,6-bis-(diethylamino)-9-(2',4'-disulfophenyl)xanthylium hydroxide sodium salt (Acid Red 52; C.I. 45 100); 7-hydroxy-8-[[4'-(phenylazo)phenyl]azo]-1,3-naphthalenedisulfonic acid disodium salt (Acid Red 73; C.I. 27 290); 2',4', 5',7'-tetrabromo-3', 6'-dihydroxyspiro[isobenzofurane-1(3H), 9'(9H)-xanthen]-3-one disodium salt (Acid Red 87; C.I. 45 380); 2',4',5', 7'-tetrabromo-4,5, 6,7-tetrachloro-3',6'-dihydroxyspiro[isobenzofurane-1 (3H), 9'(9H)-xanthen]-3-one disodium salt (Acid Red 92; C.I. 45 410); 3',6'-dihydroxy-4I,5'-diiodospiro[isobenzofurane-1 (3H),9'(9H)-xanthen]-3-one disodium salt (Acid Red 95; C.I. 45 425); Acid Red 195;Acid Blue 9 (C.I. 42 090); 2,2'-(9, 10-dihydro-9,10-dioxo-1,4-anthracenediyl) diimino]-bis-(5-methylbenzenesulfonic acid) disodium salt (Acid Green 25; C.I. 61 570); N-[4-[[4'-(dimethylamino) phenyl]-(21'-hydroxy-3'',6''-disulfo-1''-naphthyl) methylene]-2,5-cyclohexadien-1-ylidene]-N-methylmethanaminium hydroxide (Acid Green 50; C.I. 44 090); N-[4-[[4'-diethylamino)phenyl]-(2'',4 ''-disulfophenyl) methylene]-2,5-cyclohexadien-1-ylidene]-N-ethylethanaminium hydroxide sodium salt (Acid Blue 1; C.I. 42 045); N-[4-[[4'-diethylamino)phenyl]-(5''-hydroxy-2'', 4''-disulfophenyl)methylene]-2,5-cyclohexadien-1-ylidene]-N-ethylethanaminium hydroxide calcium salt (Acid Blue 3; C.I. 42 051); 1-amino-4-(cyclohexylamino)-9,10-dihydro-9,10-dioxo-2-anthracenesulfonic acid sodium salt (Acid Blue 62; C.I. 62 045); 2-(1',3'-Dihydro-3'-oxo-5'-sulfo-2'H-indol-2'-ylidene)-2,3-dihydro-3-oxo-1H-indole-5-sulfonic acid disodium salt (Acid Blue 74; C.I. 73 015); 9-(2'-carboxyphenyl)-3-[(2''-methylphenyl)amino]-6-[(2'''-methyl-4'''-sulfophenyl)amino)]-xanthylium hydroxide sodium salt (Acid Violet 9; C.I. 45 190); 2-[(9',10'-dihydro-4'-hydroxy-9',10'-dioxo-1'-anthracenyl)amino]-5-methylbenzenesulfonic acid sodium salt (Acid Violet 43; C.I. 60 730); 3,3'-[sulfonyl-bis(2-nitro-4-,1-phenylen) imino]-bis-[6-phenylamino)benzene disodium sulfonate] (Acid Brown 13; C.I. 10 410); 4-amino-5-hydroxy-3-[(4'-nitrophenyl) azo]-6-(phenylazo)-2,7-naphthalenedisulfonic acid disodium salt (Acid Black 1; C.I. 20 470); 3-hydroxy-4-[(2'-hydroxy-1'-naphthyl)azo]-7-nitro-1-naphthalenesulfonic acid sodium salt (Acid Black 52; C.I. 15 711); N-[4-[[4'-(diethylamino)phenyl]-[4''-(ethylamino)-1''-naphthyl]methylene]-2,5-cyclohexadien-1-ylidene]-N-ethylethaneammonium chloride (Basic Blue 7; C.I. 42 595); 4-[(4'-aminophenyl)-4(4'-imino-2',5'-cyclohexadien-1'-ylidene)-methyl]-2-methylaminobenzene hydrochloride (Basic Violet 14; C.I. 42 150); 4-(acetylamino)-5-hydroxy-6-[[7'-sulfo-4'-[(4''-sulfophenyl)azo]-1'-naphthyl]azo]-1,7-naphthalenedisulfonic acid tetrasodium salt (Brilliant Black 1; C.I. 28 440); [8-(p-aminophenyl)azo]-7-hydroxy-2-naphthyl]-trimethylammonium chloride (Basic Brown 16; C.I. 12 250); [8-[4'-amino-2'-nitrophenyl)azo]-7-hydroxynaphthyl]trimethylammonium chloride (Basic Brown 17; C.I. 12 251); 7-hydroxy-8-[(2'-methoxyphenyl) azo]-N,N,N-trimethyl-2-naphthylammonium chloride (Basic Red 76; C.I. 12 245); 3-[(4'-amino-6'-bromo-5',8'-dihydro-11-hydroxy-81-imino-5'-oxo-2'-naphthyl)amino]-N,N,N-trimethylammonium chloride (Basic Blue 99; C.I. 56 059).

The following developer and coupler substances are preferably used:

(A) Developer Substances 2,5-diaminotoluene, 2,5-diaminophenylethanol, p-aminophenol, 1,4-diaminobenzene, 1-methyl-2,5-p-diaminobenzene, 1-methyl-2,5-diaminobenzene, 1-amino-4-bis(2'-hydroxyethyl)aminobenzene, 2,4,5,6-tetraaminopyrimidine, 1-hydroxy-3-methyl-4-aminobenzene, 1-(2'-hydroxy ethyl) -2,5-diaminobenzene, 4-amino-2-aminoethylphenol, 4-amino-1-hydroxy-2-(2'-hydroxyethyl)aminoethylphenol, 4-hydro-2,5,6-triaminopyrimidine, 4,5-diamino-1-(4'chlorobenzyl)-pyrazole hemisulfate and 4-amino-m-cresole.

(B) Coupler Substances

Resorcinol, 4-chlororesorcinol, 4,6-dichlororesorcinol, 2-methylresorcinol, 2,4-diamino-5-fluorotoluene, 2-amino-4-(2'-hydroxyethyl)aminoanisole, 1,3-diaminobenzene, 4-amino-2-methylphenol, 2,4-diaminophenoxyethanol, 1-naphthol, maminophenol, 3-amino-4-chloride-6-methylphenol, 3-amino-2-chloride-6-methylphenol, 3-amino-fluoro-6-methylphenol, 3-amino-4-methoxy-6-methylphenol, 3-amino-2-methylphenol, 4-amino-2-hydroxyphenoxyethanol, 4-hydroxy-1,2-methylendioxybenzene, 4-(2'-hydroxy ethyl)amino-1,2-methylendioxybenzene, 2,4-diamino- 5-ethoxytoluene, 4-hydroxyindole, 3,5-diamino-2,6-dimethoxypyridine, 1-methyl-2-hydroxy-4-(2'-hydroxyethyl)aminobenzene, 1,3-bis-(2',4'-diaminophenoxy)propane, 2,4-diamino-5-methylphenetol, 2,4-diamino-5-(2'-hydroxyethoxy)toluene, 3-amino-2-methylamino-6-methoxypyridine, 5-aminofluoro-2-methylphenol hemisulfate and 2,4-diamino-5-fluorotoluene sulfahydrate.

The agent in accordance with the invention contains one or a plurality of the aforementioned direct dye compounds and/or developer and coupler substances. The dye compounds, if they are alkali-based, can also be added in form of physiologically compatible acid adding salts, for example as hydrochloride or sulfate, or provided they have aromatic OH-groups, in form of alkali-based salts, for example as alkali phenolate.

The direct dye compounds are present in the agent in accordance with the invention in a quantity of approximately 0.01 to 5 weight-percent, preferably 0.05 to 3 weight-percent.

The quantity of developer and coupler substances to be used is approximately 0.01 to 5 weight-percent, and preferably 0.1 to 3 weight-percent, each; the total quantity of both substances is then 0.02 to 10 weight-percent, particularly 0.2 to 6 weight-percent.

In general the developer substances and coupler substances are used in approximately equimolar quantities. If, however, the developer substance added is slightly in excess of or below the prescribed quantity, this does not present a disadvantage. In addition, the dye carrier composition in accordance with this invention can also contain other dye compounds for example 6-amino-2-methylphenol, 3-(2,6-diaminopyridyl-3-azo)pyridine and 2-amino-5-methylphenol.

The hair dye carrier composition in accordance with the invention is preferably available as an emulsion, a gel or particularly as a cream.

In a non-oxidative hair dye composition based on direct dye compounds, the pH-value of the hair dye composition in accordance with the invention is in the range from 5 to 10, preferably 6 to 9, while in oxidative dye carrier compositions based on a developer/coupler substance combination, the pH-value ranges from 7.5 to 12, and preferably 9 to 11, with the pH-value of the ready-to-use dye carrier composition (i.e. the mixture of the dye carrier composition in accordance with the invention and the oxidation solution) ranging from 5.5 to 10, and preferably from 6 to 9.

Depending on the composition of the desired pH-value of the dye carrier composition the pH-value range can be set preferably by means of ammonia or organic amines, for example glucamines, aminomethylpropyl alcohol, monoethanolamine, or triethanolamine, inorganic alkali, for example sodium hydroxide, potassium hydroxide, sodium carbonate or calcium hydroxide, or organic or inorganic acids, for example lactic acid, citric acid, acetic acid or phosphoric acid.

Of course, if necessary, the above-described hair dye carrier composition can have other conventional additives for coloring hair, for example preservatives and perfume oil; salts for adjusting the viscosity, for example sodium chloride or sodium sulfate; anti-oxidants, for example sodium sulfite, thioglycolic acids or ascorbic acid; complexing agents; water as solubilizers, low aliphatic alcohols, such as ethyl alcohol, propyl alcohol, isopropyl alcohol, or glycerin and 1,2-propylene glycol as glycols; wetting agents or emulsifiers of the categories of anionic, cationic, amphoteric or non-ionic surface active substances; higher fatty alcohols as thickeners, starch or cellulose derivatives; further, softeners; vaseline, paraffin oil, fatty acids as well as conditioning substances such as cationic resins, lanolin derivatives, cholesterol, vitamins, pantothenic acid and betaine. The aforementioned ingredients are used in conventional amounts generally applicable for such purposes. For example the wetting agents and emulsifiers are contained in the composition according to the invention in concentrations of 0.1 to 30 weight-percent, the thickeners in a quantity of 0.1 to 25 weight-percent and the conditioning substances in a concentration of 0.1 to 5.0 weight-percent.

Of particular advantage in this case are additions to the hair dye carrier composition in accordance with the invention of non-ionic and/or anionic wetting agents or emulsifiers, for example fatty alcohol sulfates, particularly lauryl sulfate, sodium cocoyl sulfate, ethoxylated fatty alcohol sulfates, particularly sodium lauryl ether sulfates with 2 to 4 molecular units of ethylene oxide, ethoxylated fatty acid esters, ethoxylated nonylphenols, ethoxylated fatty alcohols, alkylbenzene sulfonates or fatty acid alkanolamides, in a total quantity of approximately 0.1 to 30 weight-percent, preferably 0.2 to 15 weight-percent.

For use of the oxidative hair dye carrier composition, the above-described dye carrier composition is mixed with an oxidation solution immediately prior to dyeing the hair and a sufficient amount of the ready-to-use hair dyeing mixture, generally approximately 60 to 200 grams, is applied depending on the thickness of the hair.

Insofar as the hair dye carrier composition does not contain any oxidation dye precuser compounds (i.e. developer and coupler substances), it is also possible to apply the hair coloring agent directly to the hair without mixing it with the oxidation solution beforehand.

The mixture is allowed to react on the hair for 10 to 45 minutes at 15 to 50° C., preferable for 20 minutes at 40° C., subsequently the hair is rinsed with water and dried. If necessary, the hair is washed with a shampoo after rinsing and perhaps rinsed once more with a weak organic acid, for example tartaric acid. Subsequently the hair is dried.

The hair dye carrier composition in accordance with the invention provides an intensive, protective and gentle coloring of the hair. Because of the improved color balance, even coloring of the hair can be achieved from the undamaged hairline to the severely damaged ends of the hair.

The following examples describe the object of the invention in more detail without restrictive limitations:

EXAMPLES

Example 1

Oxidative Hair Dye Carrier Composition

| | |
|---|---|
| 15.00 g | Cetyl alcohol |
| 3.50 g | Sodium lauryl alcohol - diglycolic ether sulfate (28% aqueous solution) |
| 3.00 g | Monoethanolamine |
| 1.30 g | 2,5-Diaminotoluene |
| 1.00 g | Beeswax |
| 1.00 g | Keratin hydrolyzate |
| 0.65 g | Resorcinol |
| 0.30 g | Ascorbic acid |
| 74.25 g | Water |
| 100.00 g | |

Just prior to application, 50 g of the aforementioned hair dye carrier composition are mixed with 50 g of a 2% aqueous hydrogen peroxide solution. The obtained mixture subsequently is applied to blond natural hair. After a reaction time of 30 minutes at 40° C. the hair is rinsed with water and dried.

An even, natural, medium-blond tone is imparted to the hair, and the hair has a significantly better-conditioned appearance than can be noted with the use of the same oxidative hair dye carrier composition, but without the addition of beeswax and protein hydrolyzate.

Example 2

Oxidative Hair Dye Carrier Composition

| | |
|---|---|
| 15.00 g | Cetyl alcohol |
| 3.50 g | Sodium, lauryl alcohol - diglycolic ether sulfate (28% aqueous solution) |
| 3.00 g | Monoethanolamine |
| 1.30 g | 1-Methyl-2,5-diaminobenzene |
| 1.00 g | Beeswax |
| 0.65 g | Resorcinol |
| 0.50 g | Keratin hydrolyzate |
| 0.50 g | Silk protein hydroly#ate |
| 0.50 g | 2-Amino-6-chloro-4-nitrophenol |
| 0.30 g | Ascorbic acid |
| 74.75 g | Water |
| 100.00 g | |

The application is done in the same manner as outlined in Example 1.

An even, vibrant, glowing gold-orange tone is achieved, and the hair is virtually undamaged by the color treatment.

Example 3

Hair Tinting Composition

| | |
|---|---|
| 10.0 g | Cetyl alcohol |
| 5.0 g | Sodium lauryl sulfate |
| 1.5 g | 2-Amino-6-chloro-4-nitrophenol |
| 1.0 g | Monoethanolamine |
| 1.0 g | Beeswax |
| 0.5 g | Keratin hydrolysate |
| 0.3 g | Silk protein hydrolyzate |
| 0.2 g | Glycine |
| 80.5 g | Water |
| 100.0 g | |

The hair coloring agent is applied to the hair and after a reaction time of 20 minutes at 20° C. is rinsed with water, styled and dried.

An even, vibrant, glowing gold-orange tint is achieved.

All figures given in percent are weight-percent, unless otherwise indicated.

What is claimed is:

1. A dye carrier composition for oxidative dyeing of hair, said composition comprising a combination of about 0.01 to 5 percent by weight of developer substance and about 0.01 to 5 percent by weight of coupler substance, beeswax and at least one ingredient selected from the group consisting of protein hydrolyzates and amino acids.

2. The dye carrier composition in accordance with claim 1, containing from 0.1 to 10 percent by weight of said beeswax.

3. The dye carrier composition in accordance with claim 1, wherein said protein hydrolyzates include keratin hydrolyzates and silk protein hydrolyzates.

4. The dye carrier composition in accordance with claim 1, wherein said amino acids are selected from the group consisting of glycine, alanine, valine, leucine, glutaminic acid and arginine.

5. The dye carrier composition in accordance with claim 1, containing from 0.1 to 10 percent by weight of said at least one ingredient.

6. The dye carrier composition in accordance with claim 1, further comprising 0.1 to 30 weight percent of an non-ionic and/or anionic wetting agent or emulsifier.

7. The dye carrier composition in accordance with claim 6, wherein said non-ionic and/or anionic wetting agent or emulsifier is selected from the group consisting of fatty alcohol sulfates, ethoxylated fatty alcohol sulfates, ethoxylated fatty acid esters, ethoxylated nonylphenols, ethoxylated fatty alcohols, alkylbenzene sulfonates and fatty acid alkanolamides.

8. The dye carrier composition in accordance with claim 1, further comprising a direct-dyeing dye compound.

9. A method for oxidative dyeing of hair, said method comprising the steps of:

a) providing a dye carrier composition comprising a combination of about 0.01 to 5 percent by weight pf developer substance and about 0.01 to 5 percent by weight of coupler substance, beeswax and at least one ingredient selected from the group consisting of protein hydrolyzates and amino acids;

b) mixing said dye carrier composition with an oxidizing solution immediately prior to application to provide a ready-to-use hair dyeing mixture;

c) applying an amount of the ready-to-use hair dyeing mixture sufficient to dye the hair directly to the hair; and then d) after the applying of step c), allowing the ready-to-use hair dyeing mixture to act on the hair for a reaction time of 10 to 45 minutes at 15 to 50°C.; and e) after the allowing of step d), rinsing the hair and subsequently drying the hair.

* * * * *